United States Patent [19]

Lazzara et al.

[11] Patent Number: 5,105,690
[45] Date of Patent: Apr. 21, 1992

[54] MANIPULATOR-DRIVER FOR HOLDING AND DRIVING A SCREW-TYPE ARTICLE

[75] Inventors: Richard J. Lazzara, Lake Worth; Keith D. Beaty, West Palm Beach, both of Fla.

[73] Assignee: Implant Innovations, Inc., West Palm Beach, Fla.

[21] Appl. No.: 677,514

[22] Filed: Mar. 29, 1991

[51] Int. Cl.$^5$ ............................................. B25B 15/00
[52] U.S. Cl. .......................................... 81/436; 81/451
[58] Field of Search ........................... 81/439, 441, 451

[56] References Cited

U.S. PATENT DOCUMENTS

| | | | |
|---|---|---|---|
| 4,503,737 | 3/1985 | Di Giovanni | 81/436 |
| 4,878,406 | 11/1989 | Simpson et al. | 81/436 |
| 5,001,948 | 3/1991 | Weible et al. | 81/436 |

Primary Examiner—James G. Smith
Attorney, Agent, or Firm—Alfred H. Rosen

[57] ABSTRACT

A driver for screws, bolts and the like which have a socket for receiving the bit of a driver, in which a tapered holding section between the bit and the shaft of the driver serves to hold an article by frictional engagement with the opening edge of the socket when the bit is engaged in the socket for turning the article. The bit is shorter than the depth of the socket, and the holding section expands sufficiently away from the bit so as to make frictional contact with the edge of the socket when the bit is engaged in the socket.

11 Claims, 2 Drawing Sheets

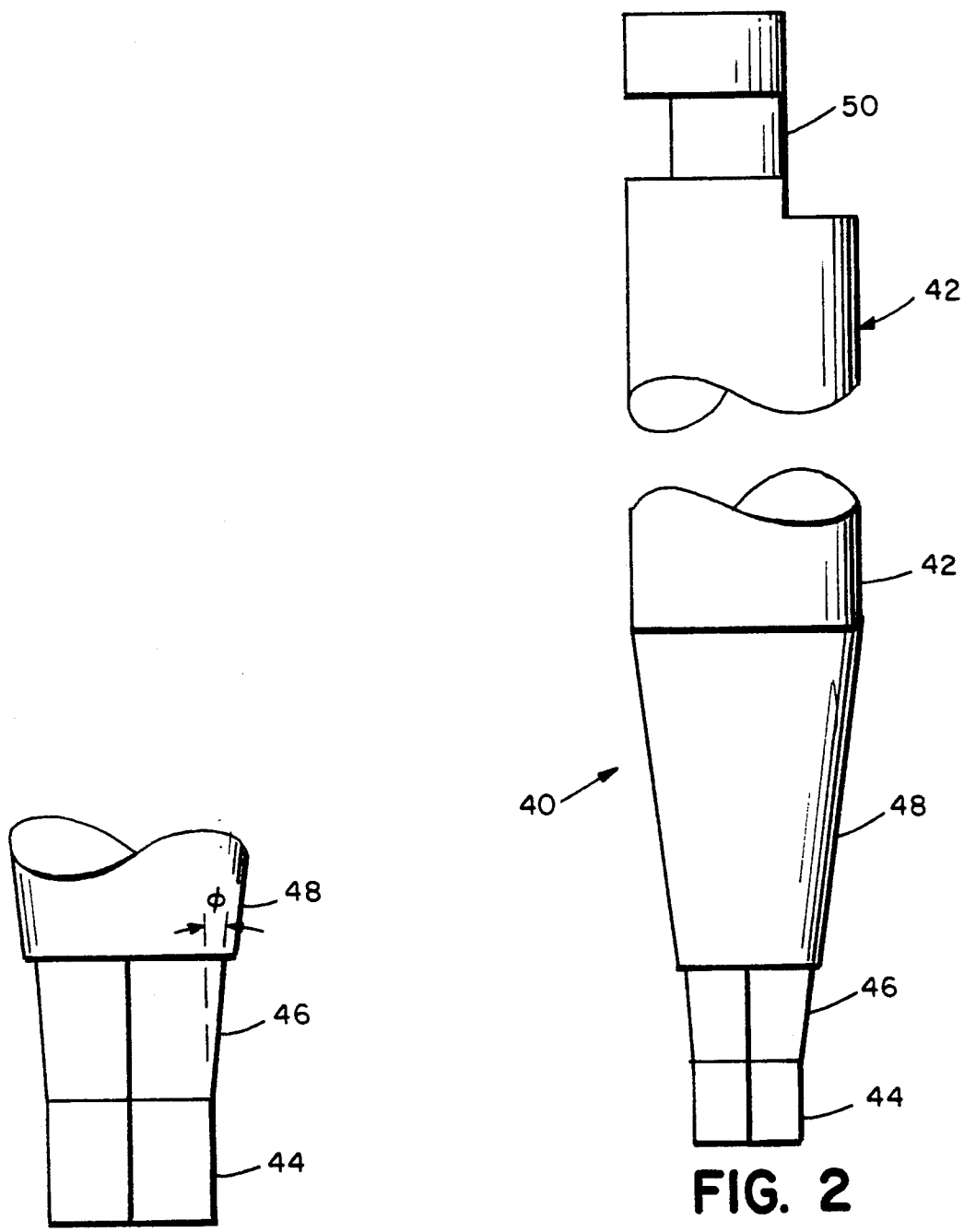
FIG. 2
FIG. 3
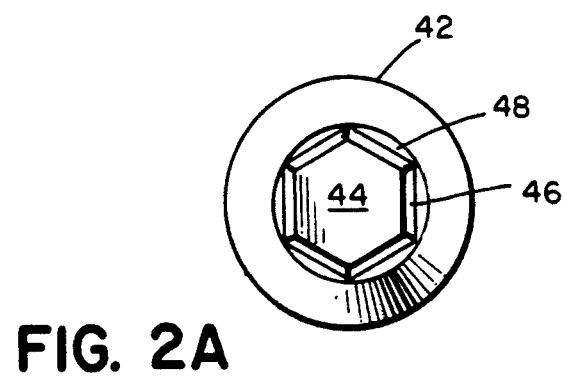
FIG. 2A

MANIPULATOR-DRIVER FOR HOLDING AND DRIVING A SCREW-TYPE ARTICLE

INTRODUCTION

In the rat of restorative dentistry it is becoming increasingly common to employ dental implant fixtures to restore the endentulous patient. This extension of restorative dentistry beyond endodontia has led to the development of implant systems providing sets of components which may be assembled with screws in the form of machine bolts which are very small. Access to implant fixtures installed in posterior locations is impeded by difficulty of access to the location as well as the layer of gingival tissue that is found surrounding the gingival aspect of the installed fixture. The risks of dropping a screw before it reaches the location of the fixture, or of cross-threading it in the opening into the fixture, are ever-present, with the result that attempts are being made to provide methods and means to hold a screw and to drive it without dropping it and without cross-threading it. The same risks and problems are present when the dental practitioner seeks to disassemble, for repair or replacement, a dental restoration based on screw-assembled implant systems. The provision of a manipulator-driver for holding and driving a screw-type article would accordingly be of great benefit to the art of restorative dentistry as extended to employing dental implant fixture systems, as well as other arts and technologies where the problems of holding and manipulating small screw-type articles for assembly and disassembly of components are encountered.

PRIOR ART

An earlier attempt to deal with this problem is described in U.S. Pat. No. 4,856,994 ('994) issued to the present inventors. There the article to be manipulated and driven is provided with a tapered socket of non-circular cross-section, and a tool is provided with a bit of similar cross-section and taper, to frictionally engage the bit in the socket for carrying purposes while allowing easy engagement of the bit in the socket so as to minimize the need for manual dexterity on the part of the dental practitioner. This system works well. However, it has been found that many practitioners seek to engage the tapered bit of the tool in sockets which do not have a matching taper. Because the sockets have very small cross-sectional dimensions (for example: 0.035" across the flats of a socket having a hexagonal cross-section), and the materials used are relatively soft (for example: titanium or gold), frictional engagement of the bit in only the edge of the opening into the socket is adequate to carry the article, but not reliably adequate to turn the article with enough force to screw it into a threaded bore intended to receive it. The bit, which is made of a harder material (for example: stainless steel) can strip away the softer material at the edge of the opening into the socket.

GENERAL DESCRIPTION OF THE INVENTION

The present invention improves the art with a manipulating tool in which the functions of carrying a screw-type article of small size, and screwing the article into a threaded bore, are separated and assigned to different parts of the same tool. The benefits of this new manipulating tool are several. It can be used with an article having a socket that is not tapered. It can frictionally engage the opening edge of the socket with sufficient strength to carry the article to or from a remote location and, using a separate part provided for driving that article in an untapered socket, it can turn the article with sufficient force to install the article in or remove the article from a threaded bore, while all the time preserving the frictional engagement between the tool and the article.

BRIEF DESCRIPTION OF THE DRAWINGS

FIGS. 2 and 2A are respective side and end views of another tool according to the invention; and FIG. 3 is an enlarged view of the bit potion of FIG. 2.

DETAILED DESCRIPTION OF THE DRAWINGS

Figures 1, 1A:
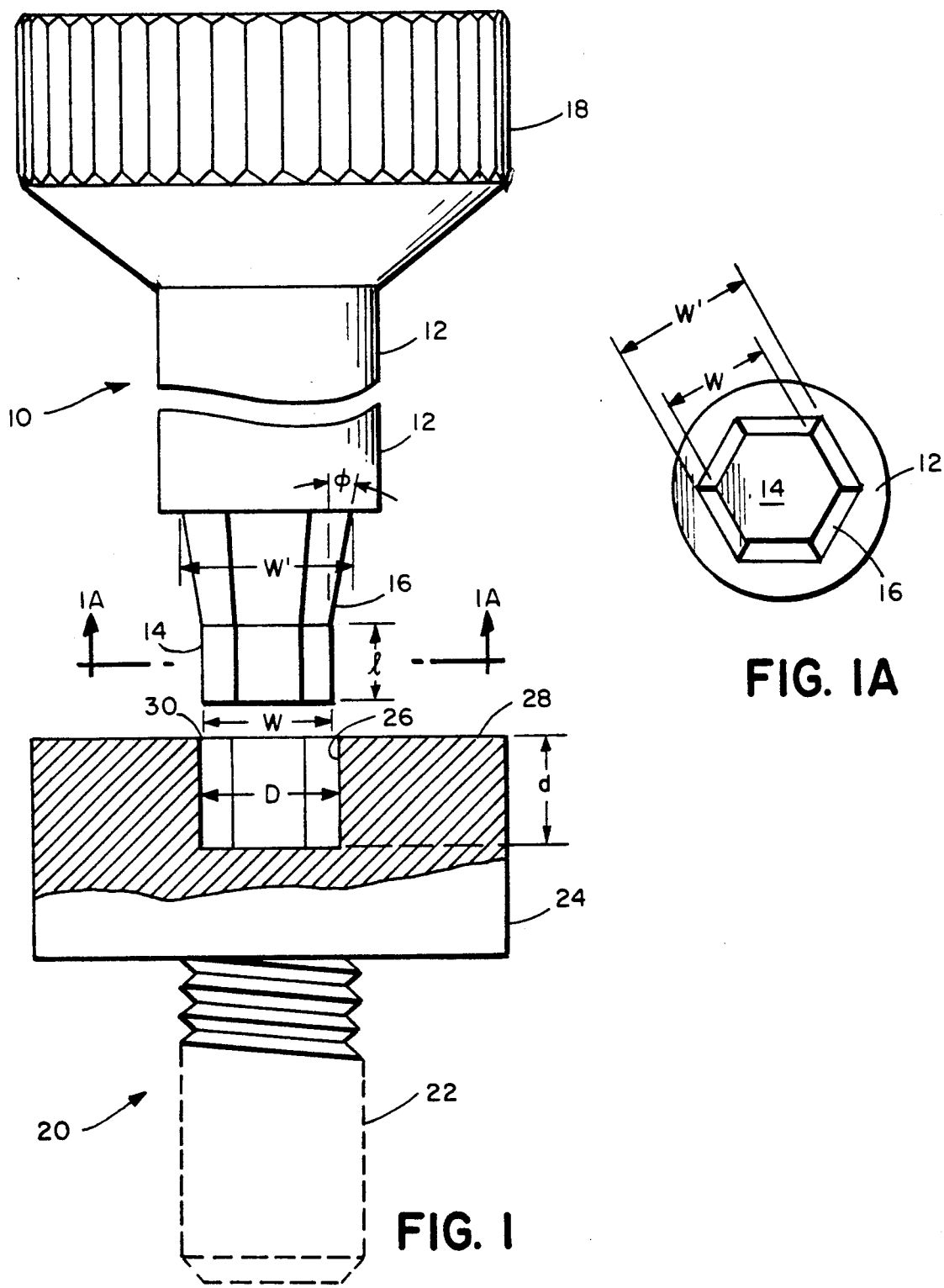
FIG. 1 is a side view, partly in section, illustrating the cooperation between a tool according to the invention and an article of the screw-type which is to be held and manipulated by the tool.
FIG. 1A is an end view of FIG. 1 on line 1A—1A.

In FIGS. 1 and 1A a tool 10 according to the invention has a shaft 12 carrying at its lower end (as seen in the drawing) a driving bit 14 and between the bit and the shaft a tapered holder section 16. The bit 14 has a hexagonal cross-section with a distance "W" between flats, and axial length "l". The tapered holding section 16 increases in cross-sectional dimension from the width W at the bit 14 to a width W' at the shaft 12, the taper being on the angle $\phi$. A manipulating knob 18 is fitted to the shaft at its top end (as seen in the drawing).

The illustrated article to be held and driven is a commonly used machine screw 20 with a threaded shaft 22 and a head 24. The head has a hexagonal socket 26 opening through its top surface 28. The width "D" of the socket between flats is preferably slightly larger than the width "W" of the bit 14. The depth "d" of the socket is greater than the length "l" of the bit 14. The width W' of the holding section 16 at the shaft 12 is greater than the width D of the socket 26.

In use, the bit 14 is inserted into the socket 26 until the holding section 16 meets the opening edge 30 of the socket at the surface 28 of the head 24. The length "l" of the bit is less than the depth "d" of the socket sufficiently to enable the tapered holding section 16 to make firm frictional engagement with the edge 30 of the socket. The width "W" of the bit 14 is sufficiently close to the width "D" of the socket to assure that the bit will be able to turn the screw 20 into a threaded bore (not shown) provided to receive it, and to unscrew the screw from such a bore. This has the advantage that the holding section 16 will not turn sufficiently in the edge 30 of the socket to wear away the edge with loss of frictional engagement. At the same time, being slightly loose in the socket, the bit 14 can be easily inserted into the socket with minimal requirement for manual dexterity. The tool of the present invention provides both reliable frictional engagement with the article to be manipulated and reliable turning of the article with sufficient force to install the article in or remove the article from a threaded bore provided to receive it while preserving the frictional engagement between the tool and the article.

Referring now to FIGS. 2, 2A and 3, the tool 40 has a main shaft 42 bearing the bit 44 at one end. The shaft tapers toward the holding section 46, in a tapered shaft section 48. As illustrated, the tapered holding section 46 and the driving bit 44 have the same hexagonal cross-sectional shape as the corresponding parts 16 and 14, respectively, in FIGS. 1 and 1A. The tapered holding section 48 is round in cross-section. The tapered holding section 46 tapers on the angle φ. The tool 40 in FIG. 2 is fitted at its other end 50 with a known engagement device for installing the tool in a dental contrangle (not shown). Thus, the embodiment of the invention shown in FIG. 2 differs from the embodiment shown in FIG. 1 in that the latter is designed for hand manipulation, while the former is designed for use in a dental contrangle.

Preferred dimensions of the tool for dental uses are:

"l+ from 0.5 mm to 1.25 mm
"W" from 0.75 mm to 2.00 mm
"φ" from 2° to 10°

These dimensions represent the best mode now known to practice the invention in the field of restorative dentistry.

The invention is not limited in scope to details of the embodiments illustrated. The holding sections 16, 46, need not be limited to the same cross-section shape as the bits 14, 44. The dimensions herein given for the best mode to practice the invention in the field of restorative dentistry are not intended to limit the invention for use in other fields or arts, so long As the bit is shorter than the socket in which it is intended to be used and the tapered holding section can frictionally engage the opening edge of the socket, such that the driver can be used to both carry the article being manipulated and turn the article with sufficient force to install it in or remove it from a host location. Conveniently, the bit may be dimensioned to fit loosely within the socket intended to receive it, as is herein illustrated, where it is desired to reduce the need for manual dexterity on the part of the user, but the invention is not limited to that feature.

We claim:

1. For use in releasably holding and driving a screw-type article having a driving socket of prescribed substantially non-circular cross-sectional shape with an opening through a surface of the article for receiving a driving bit having substantially the same cross-sectional shape, a driver comprised of a driving shaft extending along an axis, a downward-tapering holding section extending axially from one end of said shaft, and a substantially strong driving bit extending axially from said holding section, wherein said driving bit has substantially said cross-sectional shape and is dimensioned transversely to said axis to fit within the cross-sectional dimensions of said socket, the length of said bit being shorter than the depth of said socket, the width of said holding section being wider toward said shaft than a cross-sectional dimension of said socket, whereby when said bit is inserted into said socket said holding section may function to engage said article frictionally at said opening while said bit engages within said socket for turning said article around said axis.

2. A driver according to claim 1 in which the side wall of said holding section makes an angle with said axis which angle is between 2° and 10°.

3. A driver according to claim 1 in which the length of said bit is between 0.5 mm and 1.25 mm.

4. A driver according to claim 1 in which the width of said bit is between 0.75 mm and 2.00 mm.

5. A driver according to claim 2 in which the length of said bit is between 0.5 mm and 1.25 mm.

6. A driver according to claim 5 in which the width of said bit is between 0.75 mm and 2.00 mm.

7. A driver according to claim 2 in which the width of said bit is between 0.75 mm and 2.00 mm.

8. A driver according to claim 3 in which the width of said bit is between 0.75 mm and 2.00 mm.

9. A driver according to claim 1 in which said bit has a hexagonal cross-sectional shape.

10. A driver according to claim 9 in which said holding section has a hexagonal cross-sectional shape.

11. A driver according to claim 1 in which said bit is dimensioned transversely to said axis to fit loosely within the cross-sectional dimensions of said socket.

* * * * *

UNITED STATES PATENT AND TRADEMARK OFFICE
CERTIFICATE OF CORRECTION

PATENT NO. : 5,105,690

DATED : April 21, 1992

INVENTOR(S) : Richard J. Lazzara, et al.

It is certified that error appears in the above-identified patent and that said Letters Patent is hereby corrected as shown below:

```
column 1, line 6: "rat" should be --art-- column 3, line 14: "1+ should be --"1"-- column 3, line 26: "As" should be --as--"

column 4, line 6: "strong" should be --straight--
```

Signed and Sealed this

Fifteenth Day of June, 1993

Attest:

MICHAEL K. KIRK

*Attesting Officer*    *Acting Commissioner of Patents and Trademarks*